United States Patent [19]
Dolphin

[11] Patent Number: 5,916,174
[45] Date of Patent: *Jun. 29, 1999

[54] AUDIOMETRIC APPARATUS AND ASSOCIATED SCREENING METHOD

[75] Inventor: William F. Dolphin, Weston, Mass.

[73] Assignee: Sonamed Corporation, Weston, Mass.

[*] Notice: This patent is subject to a terminal disclaimer.

[21] Appl. No.: 08/797,039

[22] Filed: Feb. 10, 1997

Related U.S. Application Data

[63] Continuation of application No. 08/509,836, Aug. 1, 1995, Pat. No. 5,601,091.

[51] Int. Cl.[6] .................................................. A61B 5/00
[52] U.S. Cl. ............................ 600/559; 600/378; 73/585
[58] Field of Search .................................. 128/746, 731; 73/585; 600/379, 301, 378, 544, 555, 559

[56] References Cited

U.S. PATENT DOCUMENTS

| | | | |
|---|---|---|---|
| 4,374,526 | 2/1983 | Kemp | 128/746 |
| 4,462,411 | 7/1984 | Rickards | 128/746 |
| 4,493,237 | 1/1985 | DeLong et al. | 84/126 |
| 4,548,082 | 10/1985 | Engebretson et al. | 73/585 |
| 4,561,449 | 12/1985 | Hu et al. | 128/746 |
| 4,579,125 | 4/1986 | Strobl et al. | 128/731 |
| 4,610,259 | 9/1986 | Cohen et al. | 128/731 |
| 4,688,582 | 8/1987 | Heller et al. | 128/746 |
| 4,846,190 | 7/1989 | John | 128/731 |
| 4,884,447 | 12/1989 | Kemp et al. | 73/585 |
| 4,913,160 | 4/1990 | John | 128/731 |
| 5,003,986 | 4/1991 | Finitro et al. | 128/731 |
| 5,023,783 | 6/1991 | Cohen et al. | 364/413.02 |
| 5,081,441 | 1/1992 | Chojar | 340/384 |
| 5,098,904 | 3/1992 | Mattson et al. | 514/256 |
| 5,143,081 | 9/1992 | Young et al. | 128/741 |
| 5,230,344 | 7/1993 | Ozdamar et al. | 128/731 |
| 5,243,517 | 9/1993 | Schmidt et al. | 364/419 |
| 5,267,571 | 12/1993 | Zurek et al. | 128/746 |
| 5,372,142 | 12/1994 | Madsen et al. | 128/739 |
| 5,526,819 | 6/1996 | Lonsbury-Martin et al. | 128/746 |
| 5,601,091 | 2/1997 | Dolphin | 128/746 |

FOREIGN PATENT DOCUMENTS

WO95/15712  6/1995  WIPO.

OTHER PUBLICATIONS

Dobie et al.; "Objective response detection in the frequency domain"; Electrophysiology, 88 (1993) pp. 516–524.

Susan C. Gorin; "Special features of immittance equipment—Then and now", Hearing Instruments, 42 (8) (1991) p. 1517.

Moore et al.; "A Microcomputer–Based System for Auditory Evoked Potentials", Scand Audiol, 18 (1989) pp. 135–141.

*Primary Examiner*—Mickey Yu
*Assistant Examiner*—Dinh X. Nguyen
*Attorney, Agent, or Firm*—Testa, Hurwitz & Thibeault LLP

[57] ABSTRACT

An audiometric screening apparatus and associated method provides fast, low-cost, noninvasive screening of a subject's hearing. The apparatus includes a signal processor for generating a stimulus signal and a probe electrically coupled to the signal processor and insertible in a subject's ear. The probe includes a transmitter to transmit the stimulus signal into the ear and a receiver for receiving a first response signal from the subject's ear. An electrode, electrically coupled to the signal processor, is attached to the subject's scalp for sensing a second response signal. The signal processor processes the first response signal to provide an evoked otoacoustic emission signal and processes the second response signal to provide an auditory evoked potential signal.

29 Claims, 3 Drawing Sheets

AUDIOMETRIC APPARATUS AND ASSOCIATED SCREENING METHOD

This is a continuation Ser. No. 08/509,836 filed on Aug. 1, 1995, now U.S. Pat. No. 5,601,091.

BACKGROUND

The present invention relates generally to the field of audiometric apparatuses and associated screening methods. In particular, the invention relates to audiometric apparatuses and auditory screening methods for providing rapid, low-cost, comprehensive, non-invasive screening of a subject's hearing.

Language acquisition in infants requires a critical period of hearing capacity which spans the frequency range of human speech. The critical period extends from birth to about two to three years of age, when infants typically begin to talk with some level of proficiency.

Approximately three to five percent of newborn infants suffer from some degree of hearing impairment. These impairments can be devastating to the social, emotional and intellectual development of the affected infants. Early identification of hearing impairments in infants allows for early intervention to minimize significant speech and language deficiencies. Infants are usually unable or unwilling to participate in known behavioral auditory examinations. Moreover, delaying auditory screening until infants can verbally respond is often too late for hearing impaired infants and results in long term problems.

Federal, state and private agencies have attempted to implement universal auditory screening of infants for over twenty years. A major impediment to the implementation of universal auditory screening of infants has been the cost and complexity associated with the tests. Current infant screening tests are time consuming and require expensive devices and trained specialists to conduct the tests and interpret results. As such, universal auditory screening of infants is presently economically infeasible.

Various entities have developed audiometric devices which may be useable for screening an infant's hearing. These existing devices generally fall into one of two categories. Devices in the first category are configured to elicit auditory evoked potentials (AEPs), which are electrical responses of cells within the auditory pathway of the brain to an acoustic stimulus. Such devices typically utilize the non-invasive auditory brainstem response (ABR) test for auditory screening of infants. An earphone provides an acoustic stimulus, specifically a brief click or toneburst, to the subject's ear. Electrodes attached to the subject's scalp receive auditory evoked potentials from the scalp, which are recorded as an electroencephalogram waveform. Analysis of these brainwave patterns are used to determine if the auditory system is functioning normally.

Devices in the second category utilize the evoked otoacoustic emission (OAE) test for auditory screening. An earphone provides a brief acoustic stimulus to the subject's ear. A microphone disposed in the subject's ear adjacent the earphone receives an OAE from the ear, which is recorded as an acoustic signal. Analysis of the OAE waveform provides an indication of the functional integrity of the middle and inner ear, which together comprise the auditory periphery.

A number of limitations exist with respect to existing audiometric screening devices. One limitation is that some existing devices are complicated and require extensive training to operate. Another limitation is that other devices only provide a pass/fail indication and lack a visual display. Yet another limitation is that two separate devices are required to perform both the ABR or OAE tests. An operator typically makes a subjective determination of the acceptability of the ABR or OAE test results based on a visual examination of the response waveforms. Because existing audiometric devices do not allow for rapid, low-cost, non-invasive, comprehensive screening of infants, such devices do not adequately address the need for universal auditory infant screening.

SUMMARY OF THE INVENTION

The present invention contemplates audiometric screening apparatuses and associated methods for providing rapid, low-cost, comprehensive, non-invasive screening of a subject's hearing. An advantage of performing auditory screening using apparatuses incorporating the principles of the invention is that a behavioral response from the subject is not required. Thus, such apparatuses can be used to screen subjects who are unable to respond (e.g., infants) or unwilling or difficult to test (e.g., unconscious or mentally handicapped persons). Another advantage is that the invention is particularly useful in the area of auditory screening of infants. Except for initial infant preparation, the apparatus provides a fully automated screening procedure which includes stimulus presentation, response signal acquisition, signal analysis and interpretation of results. Nurses, technicians or hospital volunteers only require minimal training to perform auditory screening of infants. Thus, the cost of administering such auditory screening tests is reduced, encouraging universal screening of newborn infants.

The invention features an audiometric apparatus for screening a subject's hearing. The apparatus includes a signal processor for generating a first stimulus signal. A probe is electrically coupled to the signal processor and insertible in a subject's ear. The first stimulus signal comprises an amplitude modulated modulated acoustic signal which may include at least one paired tonal stimulus or at least one triple tonal stimulus. The probe includes a transmitter to transmit the first stimulus signal into the ear and a receiver for receiving a first response signal from the subject's ear. At least one electrode, electrically coupled to the signal processor, is attached to the subject's scalp for sensing a second response signal. The signal processor processes the first response signal to provide an OAE signal and processes the second response signal to provide an AEP signal. The signal processor processes the first and second signals in parallel. Moreover, the signal processor may process signals simultaneously to provide simultaneous OAE and AEP signals.

An input device is electrically coupled to a control processor to enable a user to request the signal processor to perform OAE and AEP tests. A display is electrically coupled to the control processor for displaying one or more characteristics of the OAE and AEP signals.

The apparatus may further include the capability to perform acoustic reflectivity (AR) tests. Such tests measure the degree to which sound across a range of frequencies is reflected off of the tympanum. The signal processor generates a second stimulus signal which is transmitted into the subject's ear by the transmitter. The receiver receives a third response signal from the subject's ear, and the signal processor processes the third response signal to provide a AR signal. The AR signal indicates the presence of fluid in the middle ear cavity and other pathologies.

The invention also features a portable audiometric apparatus for screening a subject's hearing. The portable apparatus includes a hand held housing and a docking station for receiving the housing. The docking station includes a battery charger for recharging the signal processor and a printer. A signal processor disposed within the housing generates a first stimulus signal. The first stimulus signal comprises an amplitude modulated signal, which may include at least one paired tonal stimulus or at least one triple tonal stimulus. A probe, electrically coupled to the signal processor, extends from the housing and is insertible into a subject's ear. The probe includes a transmitter to transmit the first stimulus signal into the ear and a receiver for receiving a first and second response signals from the subject's ear. The signal processor processes the first response signal to provide an OAE signal and processes the second response signal to provide an auditory indication signal. The auditory indication signal may be a tympanometry signal or an AR signal.

An input device electrically coupled to a control processor to enable a user to request the signal processor to perform OAE and auditory indication tests. A display is electrically coupled to the control processor for displaying one or more characteristics of the OAE and auditory indication signals.

The invention also features an auditory screening method for providing comprehensive screening of a subject's hearing. An electrode is attached to a subject's scalp. A probe, including a transmitter and a receiver, is inserted in the subject's ear. A stimulus signal is transmitted into the subject's ear. The stimulus signal comprises an amplitude modulated signal, which may include at least one paired tonal stimulus or at least one triple tonal stimulus. A response signal is received from the subject's ear via the probe. The response signal is averaged over a plurality of intervals to produce a plurality of subaverages. The subaverages are weighted based on a derived estimate of response content and combined to produce an auditory indication signal.

More specifically, the subaverages are inversely weighted based on the variance and content of the response signal. Further, the inversely weighted subaverages are combined according to the following steps: (i) performing a Fourier transform for each subaverage, (ii) determining real and imaginary components of the Fourier transform at specified frequencies, (iii) independently estimating variance of each component, and (iv) determining the probability of an auditory indication signal using an F statistic.

BRIEF DESCRIPTION OF THE DRAWINGS

These and other features of the invention are more fully described below in the detailed description and accompanying drawings of which the figures illustrate audiometric apparatuses and methods.

DETAILED DESCRIPTION OF THE INVENTION

Figure 1:
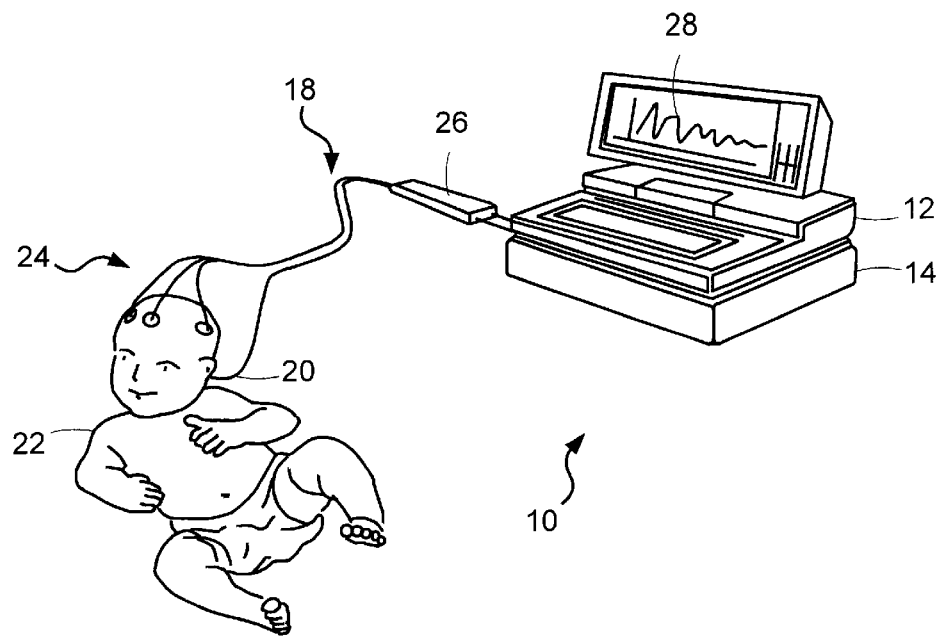
FIG. 1 is an illustration of an audiometric screening apparatus incorporating the principles of the invention.

The invention contemplates audiometric screening apparatuses for providing rapid, low-cost, comprehensive, non-invasive screening of a subject's hearing. Such apparatuses provide a fully automated screening procedure including stimulus presentation, response signal acquisition, signal analysis and interpretation of results. Thus, minimally trained personnel can perform auditory screening tests. Moreover, since such apparatuses do not require a behavioral response from the subject, they are particularly useful for screening infants, unconscious persons or mentally handicapped persons.

In one embodiment, an audiometric screening apparatus incorporating the principles of the invention is capable of performing OAE testing, ABR testing and AR testing. OAE tests take advantage of nonlinearities in the healthy auditory system in obtaining OAE signals. The procedure requires that an acoustic stimulus signal be presented to the subject's ear. The acoustic energy is conducted, via structures of the middle ear, to the fluid filled cochlea. Pressure waves propagating within the fluid result in displacements of the basilar membrane. Such displacements cause excitation of inner and outer hair cells. It is believed that, due to active processes primarily associated with length changes in outer hair cells, energy is retransmitted in a retrograde manner out of the cochlea and conducted through the middle ear to the eardrum. This retransmitted energy causes movement of the eardrum which acts as a speaker, producing acoustic energy detectable in the ear canal. Due to nonlinearities of the ear, this retransmitted sound, which is measured as an OAE, occurs at frequencies other than those present in the original stimulus.

The ABR test is a noninvasive procedure in which an acoustic stimulus signal, such as a brief click or toneburst, is presented to the subject's ear. Electrical potentials are recorded from the scalp using electrodes. In a normally functioning auditory system, a suprathreshold sound stimulates cells within the auditory pathway of the brain (primarily neurons comprising the auditory nerve and brainstem structures). This excitation spreads from the peripheral to more central structures resulting in the discharge of large numbers of neurons within the pathway. The neural activity is time-locked to the acoustic stimulus signal resulting in the synchronized discharge of large neuronal assemblies. As excitation moves through the auditory system, a sequential pattern of electrical potentials are measured from the scalp which appear as a highly stereotypical series of waves on an electroencephalogram. Analysis of these acoustically evoked brainwave patterns can be used to determine if the auditory system is functioning normally.

AR tests measure the degree to which sound across a range of frequencies is reflected off of the tympanum. An stimulus signal is transmitted into the subject's ear, and a AR response signal is received therefrom. The AR signal provides an indication of the presence of fluid in the middle ear cavity.

FIG. 1 illustrates an audiometric screening apparatus incorporating the principles of the invention. The apparatus 10 is controlled by a laptop computer 12. The computer is electrically connected to a docking station 14. A signal processor 16 (FIG. 2) disposed in the docking station generates acoustic stimulus signals in response to computer commands. A probe 18 includes an earphone 20 for presenting acoustic stimulus signals generated by the signal processor to the (infant) subject 22. The earphone also receives an OAE response signal from the subject's ear. Electrodes 24 attached to the subject's scalp sensing an ABR response signal. The response signals are amplified in a bioamplifier unit 26 and provided to the signal processor for processing and analysis. One or more characteristics of the processed OAE and AEP signals are displayed on the computer monitor 28 along with other pertinent information and other middle and inner ear pathologies.

Using a plurality of signal processing algorithms, the processed response signals are analyzed to detect the presence of a response, and, alternatively or additionally, compared with age weighted population normal signals stored in memory. If the processed response signals compare favorably with the population normal signals, the subject "passes" the screening test. If responses deviate from population normal signals by greater than a specified acceptance tolerance, the subject is "referred" for further diagnostic examinations.

The apparatus 10 may further include the capability to perform acoustic reflectivity (AR) tests. Such tests measure the degree to which sound across a range of frequencies is reflected off of the tympanum. The signal processor generates a stimulus signal which is transmitted into the subject's ear by the earphone. A third response signal from the subject's ear is received by the earphone and passed to the signal processor for processing. A processed AR signal, providing an indication the presence of fluid in the middle ear cavity, is displayed on the monitor.

Figure 2:
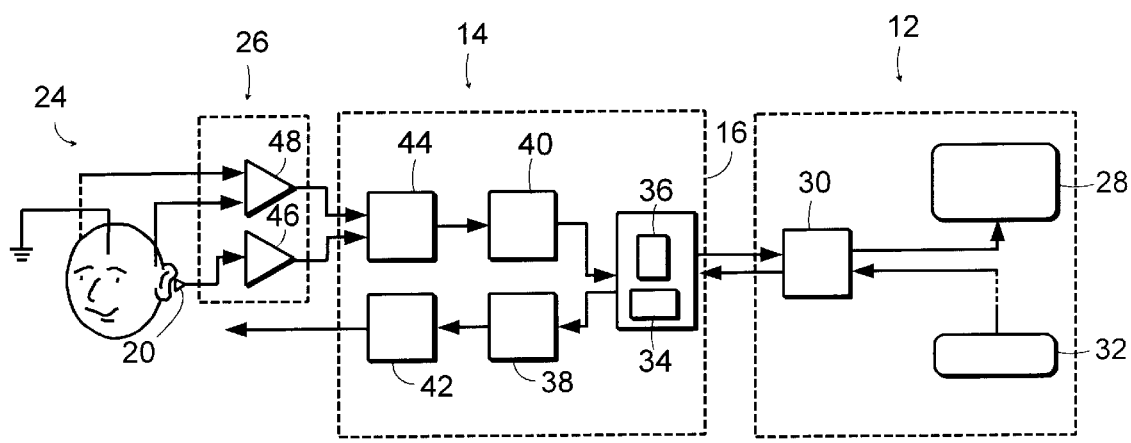
FIG. 2 is a block diagram of the audiometric screening apparatus shown in FIG. 1.

FIG. 2 is a block diagram of the audiometric screening apparatus shown in FIG. 1. The apparatus includes three main components: the computer 12, the docking station 14 and the bioamplifier unit 26. The computer includes the monitor 28, a control processor 30 and a keyboard 32. The docking station includes a signal processor 16 (which includes one or more digital signal processing (DSP) chip 34 and memory 36), analog-to-digital (A/D) converters 38, digital-to-analog (D/A) converters 40, attenuators 42 and filters 44. The bioamplifier unit includes the probe 18 and response signal amplifiers 46 and 48.

The apparatus is controlled by the computer which communicates with the docking station via an ISA bus. A safe connection between the standard 60Hz wall plug and the docking station is provided by a toroidal isolation transformer (not shown) meeting all UL 544 requirements. In one configuration, the computer includes the following components: an 86-family IBM-compatible processor, 4MB of memory, a 80 MB hard-drive, and VGA-compatible graphics card and monitor. An operator specifies the test procedure including test type(s), stimulus signal frequencies, intensities, etc. using the keyboard, a mouse or voice input.

The DSP chip 34 digital generates the acoustic stimulus signals used in the auditory tests. In one configuration, the DSP chip is a 32-bit floating point processor and the associated memory 36 includes 4MB of DRAM. The digital signal generated by the DSP is converted to analog voltage using the (16 bit) D/A converter 38 with two multiplexed channels operating at 500 kHz in single channel mode. The analog signal is passed to the programmable attenuators 42 which have attenuation range of 0.0 to 99.9 dB. The attenuated analog signal is passed to the earphone 20. The analog signal is transmitted by speakers within earphone to stimulate the auditory system of the subject In the OAE test, OAE responses to the stimulus signals are detected using a microphone disposed in the earphone. More specifically, the OAEs are evoked using two long duration, simultaneously presented pure tones. The tones are presented at frequencies $f_1$ and $f_2$. In a healthy ear, an analog response signal is remitted from the ear with significant energy at frequency corresponding to the cubic distortion product $(2f_1-f_2)$. In the AEP test, analog response signals are acquired from the scalp are detected using the electrodes 24.

In either case, the response signals from the subject are directed to the bioamplifier unit 26 which complies to UL544 and IEC601 standards. The bioamplifier unit is custom designed capable of parallel and simultaneous presentation of two acoustic stimulus signals, acquisition of OAEs from within the ear canal and AEPs from the scalp. The bioamplifier unit is fully programmable, but also has manual controls. Also, the bioamplifier unit includes an impedance meter for testing the electrode impedance used in acquisition of AEPs.

The response signals are amplified in the bioamplifier unit using separate amplifiers 46 and 48 and directed to the docking station. Within the docking station, the signals are passed through anti-aliasing filters 44 and digitized using a 16-bit A/D 40. The digitized signals are written to memory buffers in the signal processor 16, averaged by the DSP chip 34 and uploaded to the computer 12 for storage on a hard drive and display on the monitor 28.

In another embodiment, a portable hand-held audiometric screening apparatus incorporating the principles of the invention is capable of performing OAE testing, AR testing and tympanometry testing. The principles of OAE and AR testing are described above. Tympanometry tests are used to measure the acoustic admittance (or "absorption") of the tympanic membrane and middle ear system at select frequencies over a range of atmospheric pressures. Tympanometry devices typically serve as diagnostic instruments for detecting the presence of fluid in the middle ear cavity.

One primary function of the portable hand-held audiometric screening apparatus is to determine the status of the middle ear, particularly otitis media and collection of fluid in middle ear (middle ear effusion). Such conditions can seriously affect the results of audiometric tests. Middle ear status can be determined by AR otoscopy or tympanometry. It is recommended that an AR or tymanometry test be conducted immediately prior to OAE or ABR testing.

Another primary function of the portable audiometric screening apparatus is to perform OAE tests to determine whether the auditory periphery is functioning normally. In auditory screening of infants, the OAE test may be used with the objective of eliminating all babies with normally functioning auditory peripheries. Those babies that fail the initial test may be rescreened using other diagnostic tests.

Figure 3:
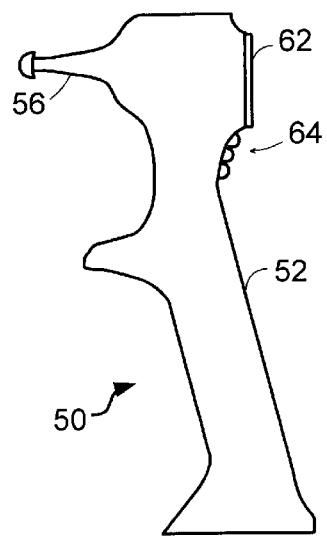
FIG. 3 is an illustration of a portable audiometric screening apparatus illustrating the principles of the invention.

FIG. 3 illustrates a portable audiometric apparatus for screening a subject's hearing. The apparatus 50 includes a hand held housing 52 and a docking station (not shown) for receiving the housing. A signal processor 54 (FIG. 4) disposed within the housing generates a first stimulus signal. The first stimulus signal comprises an amplitude modulated signal, which may include at least one paired tonal stimulus. A probe (or speculum) 56 extends from the housing and is shaped for easy insertion into a subject's ear. The probe is electrically coupled to the signal processor and includes a speaker 58 and a microphone 60. The speaker transmits the first stimulus signal into the ear, and the microphone receives one or more response signals from the subject's ear. The signal processor processes the response signals to provide an OAE signal, an AR signal and/or tympanometry signal.

An LCD screen 62 is located on the housing for displaying test results. Push button controls 64 are conveniently located on the housing for operation of the apparatus. The housing also includes batteries, recharging circuitry, data transfer circuitry, a pressure pump and air cavities.

In one configuration, the docking station simply includes a battery charger and a printer. Data from the housing is downloaded to memory and passed to the printer. In another configuration, the docking station includes the battery charger, printer, a signal processor to analyze downloaded signals, storage devices (e.g., hard disk and disk drive), serial and/or parallel ports for communication with other processors.

Figure 4:
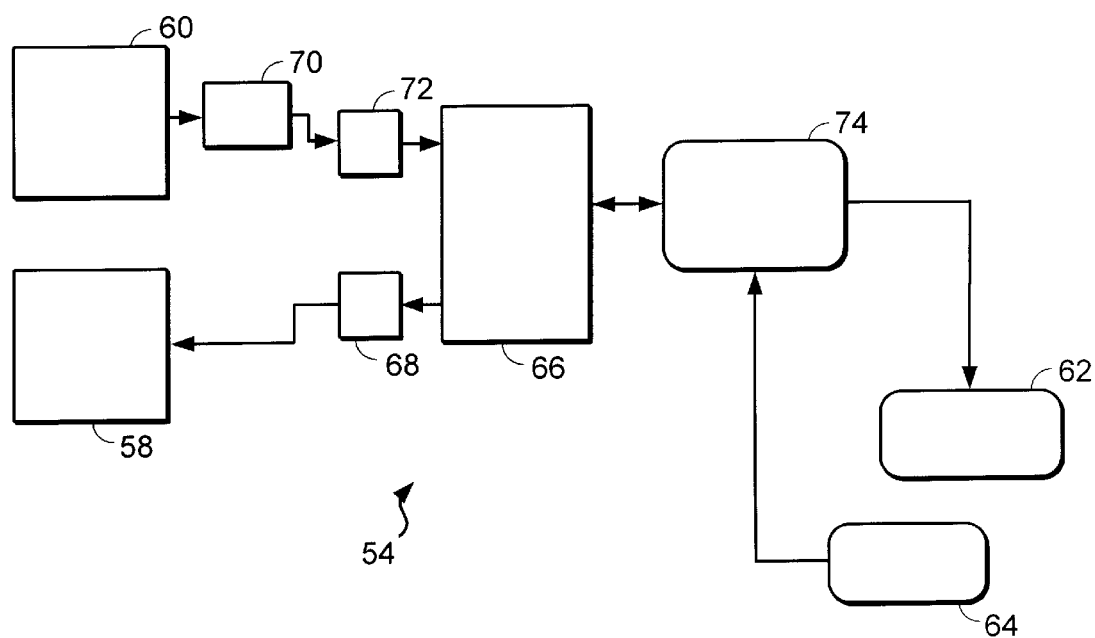
FIG. 4 is a block diagram of one embodiment of the portable audiometric screening apparatus shown in FIG. 3.

FIG. 4 is a block diagram of one embodiment of a portable audiometric screening apparatus configured to perform AR and OAE testing. To obtain AR measurements, the speculum 56 is inserted into the subject's ear canal without requiring a hermetic seal. An acoustic stimulus signal (e.g., a series of tones stepped from 226 Hz to 4520 Hz in 20 octave steps) are generated by the DSP chip 66 and converted to an analog signal by the D/A 68. The signal is briefly presented (i.e., on the order of milliseconds in duration) to the ear via the speaker 58. The microphone 60 transduces acoustic energy reflected off the tympanic membrane. This analog signal is filtered in a high-pass filter 70, digitized in the A/D 72, and averaged in the DSP chip 66.

The computer 74 Fourier transforms the processed signal and compares the reflected energy with the acoustic stimulus signal at each frequency. The level of sound reflected is calculated and a normalized value of the reflected signal (from 0.0 to 1.0) is plotted on the LCD screen 62 and stored in random-access-memory until the data is erased. At the completion of an AR test, the housing is placed within a well on the docking station. Electrical contacts on the base of the housing facilitate data transfer to the docking station for analysis, storage, printing, or retransmission to another computer or storage device.

To obtain OAE measurements, the speculum is inserted into the subject's ear canal. An acoustic stimulus signal is presented to the ear by the speaker. OAEs may be evoked using either transient or continuous stimulus signals. In the transient signal case, a brief click or tone burst is presented to the ear. A determination of the response signal is made by comparing the acoustic energy in the ear canal immediately following presentation of the stimulus signal with that obtained during non-stimulus periods.

In the continuous signal case, two pure tones (at frequencies $f_1$ and $f_2$) of extended duration are presented simultaneously. In a healthy ear, a response signal is re-emitted from the ear with significant energy at the cubic distortion product ($2f_1-f_2$). These are frequently referred to as distortion product OAEs. The distortion product of the two stimulus tones is measured and compared with the energy at that frequency in the ear canal when no stimulus is presented (i.e., the continuous background "noise floor"). Any energy at the distortion product above the noise floor is due to evoked OAEs produced by the ear. The occurrence of energy in the OAE at the frequency corresponding to this cubic distortion product is a reliable test of the functional of the middle and inner ear and an extremely efficient test for use in the initial screening. Distortion product OAEs appear to be reliable predictors of hearing loss greater than 20–30 dB normal hearing level.

Figure 5:
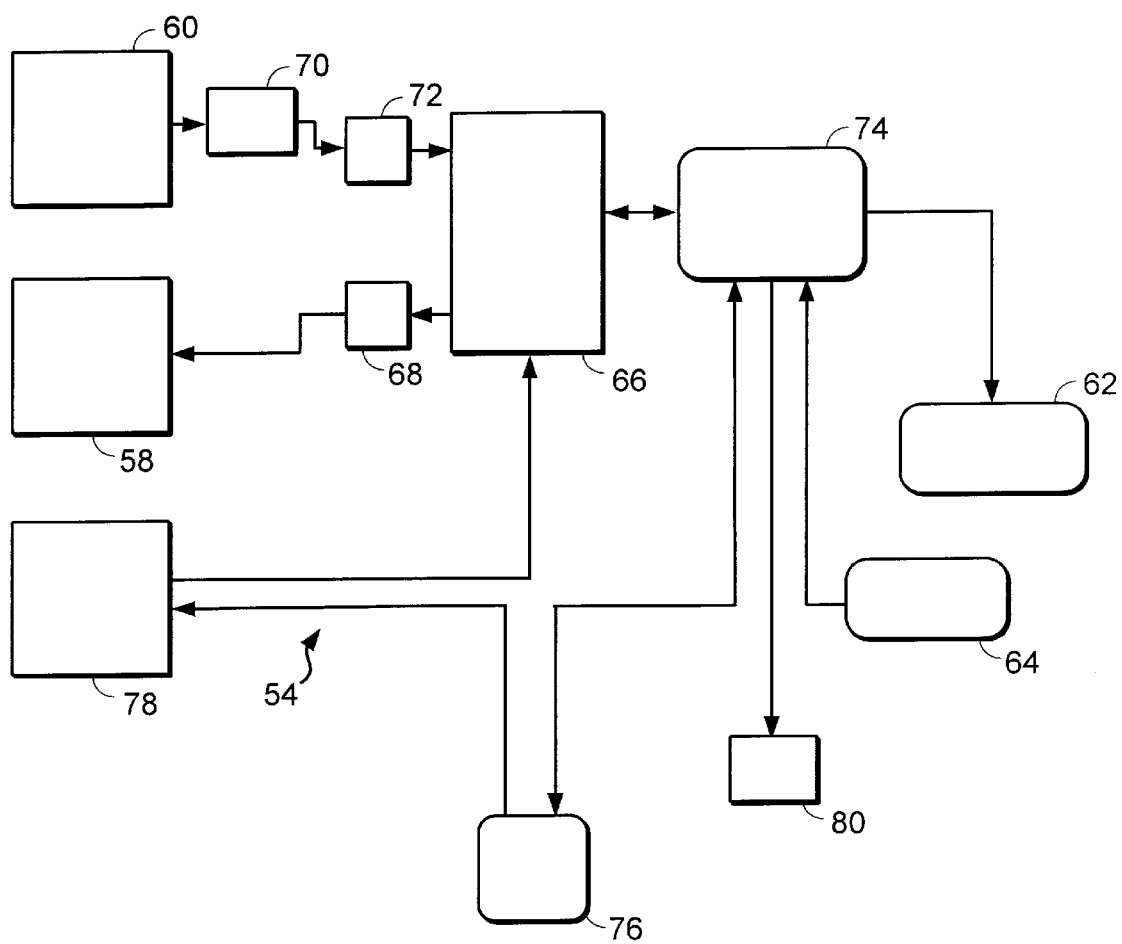
FIG. 5 is a block diagram of another embodiment of the portable audiometric screening apparatus shown in FIG. 3.

FIG. 5 is a block diagram of another embodiment of a portable audiometric screening apparatus configured to perform tympanometry and OAE testing. The OAE test capability is the same as described above. Tympanometry tests measure the admittance of the tympanic membrane and middle ear across a range of frequencies and over a range of pressures. To perform the test, the speculum is inserted into the ear. The speculum makes a pneumatic seal with the wall of the ear canal. An acoustic stimulus signal (e.g., user selectable combinations of puretones at 226 Hz and 678 Hz, and 904 Hz), is transmitted into the ear by the speaker 58. The signal reflects off the tympanic membrane at the distal end of the ear canal and is transduced by the microphone 60. A comparison of the emitted and received signals allows a calculation of the middle ear admittance at a given pressure. The pressure in the ear canal is varied from negative to positive, relative to normal atmospheric pressure, by activating a miniature pump 76 which is located in the housing and a motor 80. A pressure transducer 78 monitors pressure in the ear. The test results are displayed on the LCD screen 62 and stored in random-access-memory until the data is erased.

The invention utilizes several acoustic stimulus signals not heretofore employed for auditory screening. For example, one or more paired tonal stimuli may be used for OAE and AEP testing. In one embodiment, a paired tonal stimulus signal includes two tones having frequencies $f_1$ and $f_2$. To obtain OAE test results, a response signal is measured at the acoustic distortion product which corresponds to the frequency $2f_1-f_2$. This signal has been termed the distortion product otoacoustic emission (DPOAE). For AEP tests, the response signal includes a large component corresponding to the difference in frequency between the two tones (i.e., $|f_1-f_2|$), which is the envelope frequency of the stimulus waveform. This is termed the envelope following response (EFR).

In other embodiments, the stimulus includes multiple paired tones (e.g., $f_1$ and $f_2$, $f_3$ and $f_4$, $f_5$ and $f_6$). Such a signal can be used to simultaneously test at each of the frequency regions corresponding to the paired tones. For instance, if one used three paired tones of $f_1=1000$ Hz and $f_2=1040$ Hz, $f_3=3000$ Hz and $f_4=3070$ Hz, and $f_5=5000$ Hz and $f_6=5080$ Hz, hearing sensitivity can be tested simultaneously at 1000, 3000, and 5000 Hz.

A number of signal processing methods are employed in apparatuses incorporating the principles of the invention. For example, one method provides improved signal-to-noise ratio (signal-to-noise ratio) resulting in higher quality test results. For AEP and OAE tests, the evoked response (ER) is often small compared to the background noise (background noise). A high background noise level can make detection of the desired evoked response signal unreliable. A traditional solution to the signal-to-noise ratio problem has been to employ a combination of filtering, artifact rejection, and ensemble averaging. In the instant situation, the evoked response and background noise have overlapping spectra, so filtering offers only very little improvement in the signal-to-noise ratio. Artifact rejection improves the signal-to-noise by rejecting, and thereby excluding from the averaging process, sweeps which exceed some preset voltage threshold level. Sweeps which contains a large artifact (e.g., potentials resulting from brief muscle activity or loud noises such as coughing) are not be included in the average if it exceeds the reject threshold level. However, it is difficult to know a priori the optimal setting for the reject level because the background activity level is not stationary. This uncertainty limits the effectiveness of the artifact rejection technique in improving the signal-to-noise ratio. Therefore, filtering and artifact rejection techniques do not significantly increase the signal-to-noise ratio of the evoked response.

The invention utilizes an ensemble averaging technique in the time domain for improving the signal-to-noise ratio. A signal S(t) is recorded (from the electrodes or ear canal microphone) that includes the desired evoked response ER(t) (a deterministic signal) and background noise BN(t) (a non-stationary random process). The signal S(t) is averaged over (m) sweeps, but since the evoked response is deterministic (i.e., it does not change in amplitude, latency, or morphology over the (m) sweeps):

$$S(t)M = ER(t)M + BN(t)M \quad (1)$$

Using a the signal-to-noise ratio estimate based on the evoked response/background noise ratio, and recognizing that the evoked response and background noise may not be totally uncorrelated, it can be shown that the magnitude of the averaged acquired signal S(t) is a function of the signal-to-noise ratio and proportional to the magnitude of the averaged background variance. Since the magnitude of S(t) is a function of the signal-to-noise ratio and background noise level, and since background noise can vary from sweep to sweep, the response signal-to-noise ratio can be maximized by expressing the variance in a single sweep or, better, in a block consisting of the average of m sweeps, relative to the estimated variance of the averaged background noise. The contribution of each block is weighted inversely to this variance ratio (i.e., individual components used in the averaging process are weighted according to their individual precision).

Using AEPs and OAEs, the foregoing is applied by assuming that (as set forth in Equation (1)) the background noise is a non-stationary, Gaussian distribution with variance changing over the course of the acquisition process. Because the acquired signal is the sum of the desired evoked response (constant) and background noise (random), the precision of an individual block average is inversely proportional to the magnitude of the signal variance. Thus, the precision of each block of sweeps, along with the subsequent weighting in the averaging process, is determined as the variance of that block relative to the estimated variance of the entire average. In one implementation, if S(t) is the time waveform of the block (i.e., the average of (m) sweeps), and V is the estimated variance of the background noise after ith block, the estimate of the evoked response after the Mth average will be:

$$ER_M = (S(t)_1/V_2 + S(t)_2/V_2 + \ldots + S(t)^M/V_M) * 1/C^M \text{ where } C_M = 1/V_1 + 1/V_2 + \ldots + 1/V_M \quad (2)$$

This estimate is obtained by adding together the averaged time waveforms from each block after dividing by their corresponding variances and multiplying this sum by $1/C_M$, obtained by combining all the variances, hence:

$$ER_M = 1/M[S(t)_1/V_1 + S(t)_2/V_2 + \ldots + S(t)_M/V_M]M/C_M \quad (3)$$

This may be contrasted with the "normal" ensemble average:

$$ER_M = 1/M[S(t)_1 + S(t)_2 + \ldots + S(t)M] \quad (4)$$

The difference is that in "normal" averaging each block is given equal weight (i.e., independent of the level of background noise in that block), whereas in the current estimate the ith block is weighed inversely proportional to the level of the background noise in that block. When the background noise is constant across blocks, then the two estimates are identical. When the background noise varies, however, the current technique (by minimizing the contribution of noise-contaminated sweeps) yields a significantly improved estimate of the evoked response by increasing the signal-to-noise ratio.

As noted previously, the evoked response is typically buried in the background noise. Many techniques for the detection of AEPs utilize time-domain analysis of the transient evoked ABR waveform. Although detection of OAEs is typically performed in the frequency domain, only magnitude information of identified Fourier components is utilized. In the following technique, the relation between real and imaginary parts of Fourier components is fully utilized.

In steady-state AEP or OAE testing, each block of sweeps yields an evoked response to a periodic stimulus signal. Since the evoked response is also periodic, it may be described by its Fourier components. In auditory tests measuring AEPs in response to amplitude modulated stimuli, the response at the frequency corresponding to the stimulus envelope (i.e., the EFR) is determined. Similarly, in DPOAE tests the response at the distortion component corresponding to $2f_1 - f_2$ is measured. At these frequencies, the Fourier component is a complex number z which can be expressed in a Cartesian representation z=x+iy. Further, the values x and y represent the cosine and sine components of the evoked response. This formulation makes explicit the notion that z is a vector in the x,y, plane. With multiple estimates of z, a cluster of vectors is built up in the complex plane. The pooled estimate of the evoked response lies in the center of the cluster, and the reliability of the pooled estimate is indicated by the degree of scatter. Estimation of the amount of scatter within the cluster should provide an index of the extent that the true evoked response may deviate from the mean of the observed response.

In audiometric tests, responses to a stimulus are collected in M blocks, with each block consisting of the average of (m) individual sweeps. Thus, a set of M estimates of the Fourier component z corresponding to the frequency of the stimulus waveform envelope is made available. To determine whether evoked response is present, it must be determined whether these estimates are consistent within an "a priori" value. The M estimates of this Fourier component can be denoted by $z_1, z_2, \ldots, z_{M2}$ their empirical mean value by $z_{est} = (\Sigma z_j)/M$, and an "a priori" hypothetical value by $\zeta$. Each of the quantities $z_j$, $z_{est}$ and $\zeta$ are complex numbers, decomposable into real and imaginary parts: $z_j = x_j + iy_j$; $z_{est} = x_{est} + iy_{est}$; and $\zeta = \xi + i\eta$. From the scatter of individually determined components $z_j$ about their mean, with each of the deviations $x_j - x_{est}$ and $y_j - y_{est}$, providing one estimate, an estimate of the individual population variance is made:

$$V_{ind} = [\tfrac{1}{2}(M-1)]\Sigma[(x_j - x_{est})^2 + (y_j - y_{est})_2] = [\tfrac{1}{2}(M-1)]\Sigma[z_j - z_{est}]^2 \quad (5)$$

which is independent of the assumed population mean $\zeta$.

A second estimate, referred to as the group variance, is dependent on $\zeta$. Because the real and imaginary parts of $z_{est}$ are independently distributed and unconstrained by $V_{ind}$, a second group variance estimate is as follows:

$$V_{group} = [M/2][(x_{est} - \xi)^2 + (y_{est} - \eta)_2] = [\tfrac{1}{2}(M-1)][z_{est} - \xi]_2 \quad (6)$$

The estimate of the Fourier component for each block of (m) samples, $z_j$, are subsamples of a population whose mean is $\zeta$, and the quantities $V_{ind}$ and $V_{group}$ are estimates of the overall variance derived from independent quantities. Therefore, the ratio $V_{group}/V_{ind}$ is distributed according to the F distribution. Based on this variance ratio, a statistical approach is utilized wherein:

$$R = (1/M)(V_{group}/V_{ind}) = (M31\ 1)\ ([z_{est}\xi]^2/\Sigma[z_j - z_{est}]^2) \quad (7)$$

Therefore, for M independent estimates of Fourier components $z_j$, drawn from a sample of assumed mean $\zeta$, M●R is distributed according to $F_{[2,2M-2]}$.

This statistic, unlike other methods, fully utilizes the independence of the real and imaginary parts of the Fourier component of interest and is used for detecting the presence of a response by determining if the observed set of Fourier components $z_j$, at the frequency corresponding to the stimulus envelope or cubic distortion product, is consistent with random fluctuations alone (i.e., no response signal), or whether the set of observations implies, to within a given confidence level, that a response component is present.

In conducting audiometric studies using AEPs or OAEs, a standard procedure has been to specify that a fixed number of sweeps be acquired. However, as noted above, in situations in which the subject is quiet, with relatively low background noise, or when the stimulus is considerably above threshold, a large evoked response will be recorded with a correspondingly high signal-to-noise ratio. Thus, only relatively few sweeps are required to obtain an acceptable response. Alternatively, in situations where the subject is noisy (either episodic or during an entire test session), or where the stimulus is close to threshold, then the response is smaller or buried in larger noise, with a resultant lowered signal-to-noise ratio. In these conditions, a large number of sweeps may be required. If the artifact rejection threshold is set sufficiently low to exclude such episodic noise, or if the subject displays a sustained period of relatively high noise level, then no sweeps need be added to the accumulating buffer for averaging. By lowering the reject threshold, fewer noise-contaminated sweeps are included in the average (yielding in a higher signal-to-noise ratio), but this is at a cost of greatly prolonging the test time required to achieve a preset number of sweeps. The specification of a fixed number of sweeps is clearly an inefficient approach. In some instances, the number may be excessive (needlessly prolonging the test) or insufficient (thereby yielding an unacceptably low signal-to-noise ratio). It is quite difficult to predict "a priori" the number of sweeps required to achieve a given signal-to-noise ratio just as it is quite difficult to preset an optional artifact rejection level. However, a "a priori" the number of sweeps required to achieve a given signal-to-noise ratio just as it is quite difficult to preset an optional artifact rejection level. However, a means to estimate the quality of the obtained evoked response on an ongoing basis is available from the variances already calculated. The ratio of the variance of the averaged response block to the estimated variance of the ongoing background noise can be treated as an F-distribution:

$$F_q = VAR(ER(t))/VAR(N(t)) \quad (8)$$

In automating the test, stimulus presentation and response acquisition continues until a prespecified criterion value for acceptance is met.

The signal processing described above, although widely applicable for use with a variety of stimulus signal types, is particularly useful in facilitating acquisition and detection of responses using DPOAE and EFR tests described above. The hardware and software of the present system makes possible the acquisition and automated detection of both DPOAEs and AEPs simultaneously.

EQUIVALENTS

While the invention has been particularly shown and described with reference to specific preferred embodiments, it should be understood by those skilled in the art that various changes in form and detail may be made therein without departing from the spirit and scope of the invention as defined by the appended claims.

I claim:

1. An audiometric apparatus comprising:
   a probe insertible in a subject's ear, the probe including (i) a transmitter for transmitting a first stimulus signal into the subject's ear and (ii) a receiver for receiving a first response signal from the subject's ear;
   an electrode attachable to the subject's scalp for sensing a second response signal from the subject's scalp; and
   a signal processor electrically coupled to the probe and the electrode for processing the first response signal to provide an evoked otoacoustic emission signal and processing the second response signal to provide an auditory evoked potential signal.

2. The apparatus of claim 1 wherein the first stimulus signal comprises an amplitude modulated signal.

3. The apparatus of claim 1 wherein the first stimulus signal comprises at least one paired tonal stimuli.

4. The apparatus of claim 1 wherein the signal processor processes the first and second response signals in parallel.

5. The apparatus of claim 4 wherein the signal processor processes the first and second response signals simultaneously.

6. The apparatus of claim 1 wherein the transmitter transmits a second stimulus signal into the subject's ear, the receiver receives a third response signal from the subject's ear, and the signal processor processes the third response signal to provide an acoustic reflectivity signal.

7. The apparatus of claim 1 wherein the first stimulus signal comprises a transient signal.

8. The apparatus of claim 1 further comprising:
   a digital signal processing element;
   a memory electrically coupled to the digital signal processing element;
   a digital-to-analog converter electrically coupled to the digital signal processing element for converting the first stimulus signal from a digital format into an analog format;
   an attenuator electrically coupled to the digital-to-analog converter for regulating the first stimulus signal;
   a filter electrically coupled to the receiver and the electrode for filtering the first and second response signals;
   an analog-to-digital converter electrically coupled to the filter for converting the first and second response signals from an analog format into a digital format for the digital signal processing element.

9. The apparatus of claim 8 further comprising:
   a first amplifier electrically coupled to the probe for providing amplified first response signals to the filter; and
   a second amplifier electrically coupled to the electrode for providing amplified second response signals to the filter.

10. The apparatus of claim 1 further comprising:
    a control processor for requesting an evoked otoacoustic emission signal and an auditory evoked potential signal;
    a display electrically coupled to the control processor for displaying one or more characteristics of the evoked otoacoustic emission signal and the auditory evoked potential signal; and
    an input device electrically coupled to the control processor to enable a user to request the evoked otoacoustic emission signal and the auditory evoked potential signal.

11. An auditory signal processing method comprising:
    inserting a probe in a subject's ear;
    transmitting a stimulus signal into the subject's ear via the probe;
    receiving a response signal from the subject's ear; and
    averaging the response signal over a plurality of intervals to produce a plurality of subaverages;
    inversely weighting each subaverage; and
    combining the inversely weighted subaverages to produce an auditory indication signal.

12. The method of claim 11 wherein the auditory indication signal is an evoked otoacoustic emission signal and or an auditory evoked potential signal.

13. The method of claim 11 wherein the stimulus signal comprises an amplitude modulated signal or a transient signal.

14. The method of claim 11 further comprising inversely weighting each subaverage based the variance and content of the response signal.

15. The method of claim 11 wherein the combining step comprises averaging the inversely weighted subaverages to produce an auditory indication signal.

16. The method of claim 15 wherein the combining step comprises:

performing a Fourier transform for each subaverage;

determining real and imaginary components of the Fourier transform at specified frequencies;

independently estimating variance of each component; and determining the probability of an auditory indication signal using an F statistic.

17. A bioelectrical signal processing method comprising:

attaching a sensor to a subject;

transmitting a stimulus signal into the subject;

receiving a response signal from the subject via the sensor; and averaging the response signal over a plurality of intervals to produce a plurality of subaverages;

inversely weighting each subaverage; and combining the inversely weighted subaverages to produce a biolelectrical signal.

18. The method of claim 17 wherein the sensor is an electrode.

19. The method of claim 17 wherein the sensor is a probe.

20. The method of claim 17 wherein the bioelectrical signal is an auditory signal.

21. The method of claim 20 wherein the auditory indication signal is an evoked otoacoustic emission signal and or an auditory evoked potential signal.

22. The method of claim 17 wherein the stimulus signal comprises an amplitude modulated signal.

23. The method of claim 17 wherein the stimulus signal comprises a transient signal.

24. The method of claim 17 further comprising inversely weighting each subaverage based the variance and content of the response signal.

25. The method of claim 17 wherein the combining step comprises averaging the inversely weighted subaverages to produce the bioelectrical signal.

26. The method of claim 25 wherein the combining step comprises:

performing a Fourier transform for each subaverage;

determining real and imaginary components of the Fourier transform at specified frequencies;

independently estimating variance of each component; and determining the probability of the biolelectrical signal using an F statistic.

27. An automated bioelectrical signal processing method comprising:

a) attaching a sensor to a subject;

b) transmitting a stimulus signal into the subject;

c) receiving a response signal from the subject via the sensor; and d) averaging the response signal over a plurality of intervals to produce a plurality of subaverages;

e) inversely weighting each subaverage;

f) performing a Fourier transform for each subaverage;

g) determining real and imaginary components of the Fourier transform at specified frequencies;

h) analyzing the components to determine the presence of (1) a biolelectrical signal and random noise, or (2) only random noise; and i) repeating steps b) to h) if the components are indicative of only random noise.

28. A signal processing apparatus comprising:

a probe insertible in a subject's ear, the probe including (i) a transmitter for transmitting a first stimulus signal and a second stimulus signal into the subject's ear, and (ii) a receiver for receiving a first response signal and a second response signal from the subject's ear; and a signal processor electrically coupled to the probe for processing the first response signal to provide an evoked otoacoustic emission signal and processing the second response signal to provide an auditory indication signal.

29. The apparatus of claim 28 wherein the auditory indication signal is a tympanometry signal or an acoustic reflectivity signal.

* * * * *